(12) United States Patent
Wortrich

(10) Patent No.: US 6,923,821 B2
(45) Date of Patent: Aug. 2, 2005

(54) MICROKERATOME BLADES AND METHODS OF MAKING

(76) Inventor: Theodore Wortrich, 5 Ocean Ridge Dr., Newport Coast, CA (US) 92657

(*) Notice: Subject to any disclaimer, the term of this patent is extended or adjusted under 35 U.S.C. 154(b) by 123 days.

(21) Appl. No.: 10/085,190

(22) Filed: Feb. 27, 2002

(65) Prior Publication Data

US 2002/0143351 A1 Oct. 3, 2002

Related U.S. Application Data

(60) Provisional application No. 60/272,021, filed on Feb. 28, 2001.

(51) Int. Cl.[7] ............................................. A61F 9/00
(52) U.S. Cl. ................................ 606/166; 600/452
(58) Field of Search ............................... 606/170, 171, 606/169, 167, 168, 166, 172, 173; 604/22; 600/452

(56) References Cited

U.S. PATENT DOCUMENTS

| | | | |
|---|---|---|---|
| 4,662,370 A | 5/1987 | Hoffmann et al. | |
| 4,884,570 A | 12/1989 | Krumeich et al. | |
| 4,917,086 A | 4/1990 | Feltovich et al. | |
| 5,133,726 A | 7/1992 | Ruiz et al. | |
| 5,215,104 A * | 6/1993 | Steinert | 128/898 |
| 5,342,378 A | 8/1994 | Giraud et al. | |
| 5,586,980 A * | 12/1996 | Kremer et al. | 606/4 |
| 5,807,380 A * | 9/1998 | Dishler | 606/5 |
| 5,817,115 A * | 10/1998 | Nigam | 606/166 |
| 6,051,009 A | 4/2000 | Hellenkamp et al. | |
| 6,126,668 A * | 10/2000 | Bair et al. | 606/166 |
| 6,350,272 B1 * | 2/2002 | Kawesch | 606/166 |
| 6,506,198 B1 * | 1/2003 | Amano | 606/166 |
| 6,527,788 B1 * | 3/2003 | Hellenkamp | 606/166 |

* cited by examiner

Primary Examiner—Julian W. Woo
Assistant Examiner—Victor X Nguyen
(74) Attorney, Agent, or Firm—Jone Tullar & Cooper PC

(57) ABSTRACT

A blade and holder combination for use with a microkeratome, and including means for improving mechanical stability when the blade is reciprocated during cutting, as well as a peripheral configuration minimizing local nonuniformities. Blades in accordance with the invention have a generally hemispherical posterior geometry that include an adjacent centralized ovoid coupling aperture and a small centrally disposed access slot that may include indicia for denoting blade type. The hemispherical geometry minimizes both local deformities and the processing needed to assure that the product functions to provide a clean, uniform surgical result.

2 Claims, 3 Drawing Sheets

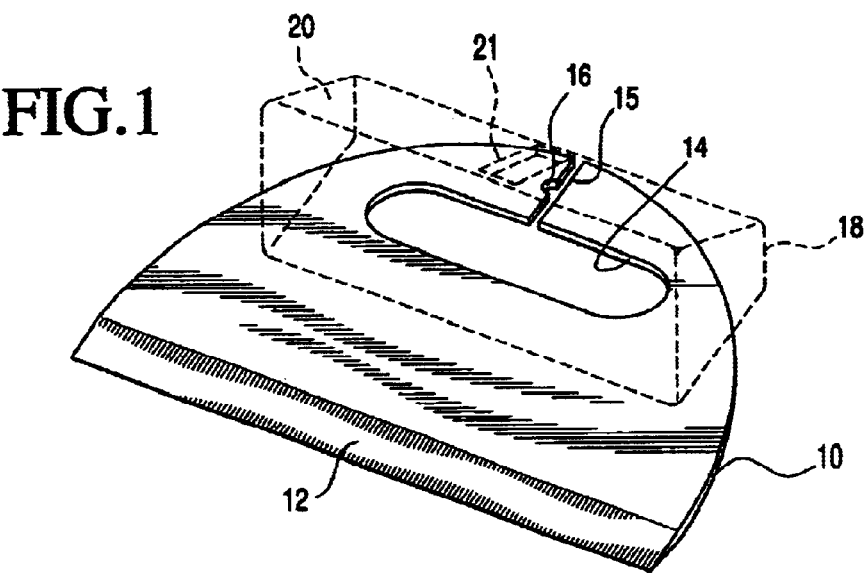
FIG.1
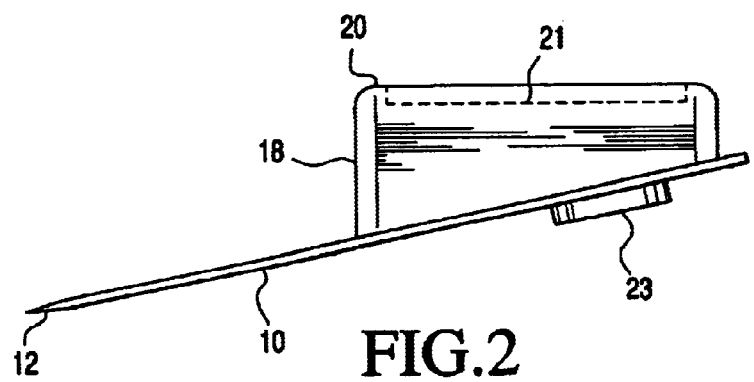
FIG.2
FIG.3
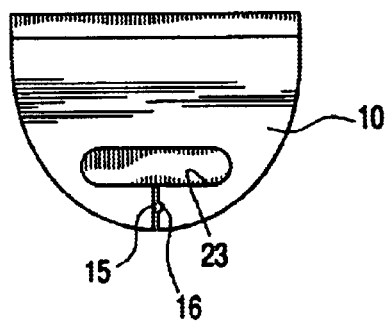
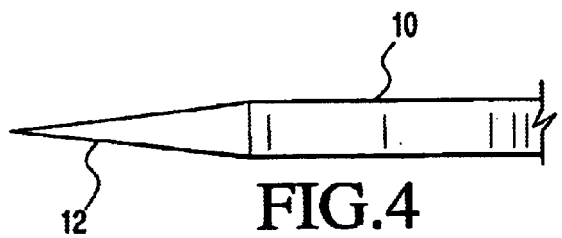
FIG.4

MICROKERATOME BLADES AND METHODS OF MAKING

This application claims benefit of application Ser. No. 60/272,021 filed on Feb. 28, 2001.

BACKGROUND OF THE INVENTION

This invention relates to blades and blade drive combinations for ophthalmic surgical procedures and more particularly to improved blades and blade holders for use in microkeratomes, and methods of making such blades.

A very widely adopted modern technique for correction of deficiencies in human vision is based on a procedure which modifies the optics of the cornea. In this procedure, generally termed laser in-situ keratomileusis (LASIK), a flap is cut in the cornea. The flap is lifted and the exposed area is impacted by a laser beam in a precision pattern to ablate or vaporize small target areas on the cornea in accordance with the needed correction. The flap is immediately returned into its position, where it stays in place without the use of stitches or sutures.

The instruments for making the cuts are called microkeratomes and comprise semiautomatic or automatic units for first suctioning the eye surface into stable position for the cutting blade, and then for slicing the blade through the cornea at the precise chosen depth. The actual surgical procedure is of short duration, presents low risk and involves minimal recovery time. Because of these factors earlier procedures for reshaping the cornea have largely been supplanted by the LASIK procedure, except where the LASIK procedure cannot be used for a particular optical correction.

The use of microkeratomes is generally regarded as having originated with Barraguer, based on publications dating from 1949, which initially used a manually driven device. While the subsequent history of development is relatively short, it has been intense, leading to a number of machines that are now in existence. All essentially employ a small thin cutting blade (e.g. about 0.01 inch in thickness) that has a cutting edge width of the order of one half inch (12.5 mm). The blade is held at a low angle to slice through the cornea at the selected depth. Even though the cutting edge of the blade is very sharp, it is reciprocated or oscillated from side to side during the advance through the cornea to facilitate the shearing action. In most machines, starting with those of Barraguer, this reciprocation is accomplished by an eccentric drive pin on the machine that engages a slot in a holder or driver attached to the blade. As the eccentric drive pin rotates during advance of the blade, it moves along the slot or groove, which is sized and angled so that transverse displacements of the eccentric pin introduces the reciprocating motion. The holder is attached permanently, or in a securely detachable manner, to the upper side of the cutting blade, and the slot is at an angle to the plane of the blade, which angle is determined by machine design. That is, the reciprocating pin lies, dependent upon system configuration, along an axis that may be close to or at a substantial angle relative to the horizontal.

The Barraguer design is shown in Hoffman U.S. Pat. No. 4,662,370, with other designs being shown in Ruiz U.S. Pat. No. 5,133,726, Krumeich U.S. Pat. No. 4,884,570, and Giraud et al. U.S. Pat. No. 5,342,378. The referenced patents position the blade at a relatively small acute angle relative to the cornea, with the reciprocating pin rotating about an axis at a substantially higher angle. In accordance with these teachings the blade is driven in a linear path through the cornea as the cut is made. To provide a microkeratome which drives the blade in an arc about the center of the eye, Hellenkamp in U.S. Pat. No. 6,051,009 uses a blade and holder combination, also in conjunction with an eccentric drive pin, but one that rotates about a substantially vertical axis. Thus the slot or groove in the blade holder is on the top surface of the holder, lying in a horizontal plane. The Hellenkamp machine design is such that, given the arcuate movement, the rear corners of a rectangular blade would interfere with other parts. To avoid this, the rear corners of the blade are simply eliminated, making the rear edge shorter than the front cutting edge of the blade. Apart from this geometrical difference, the blades of Hellenkamp and the different prior microkeratomes must meet the same basic requirements as to size, thinness, sharpness of blade edge, and the like.

Microkeratome blades are not per se fragile, in the ordinary sense of the term, but are so subject to minor flaws that they can be regarded as virtually unusable after any minor impact or deviation. The medical procedures involved, and the results sought, must be so controlled that a blade used in making an incision in one eye is typically not used again, because the blade tip has deteriorated merely from its brief engagement with corneal tissue. In further evidence of this criticality, some of the microkeratome machines include sensors for measuring frictional and other drag exerted on the vibratory mechanism. If the resistance is too high the drive might vibrate, affecting the cleanness of the incision. The drag of the cutting blade is a minor factor in this dynamic, but the use of such a measurement indicates the degree of uniformity that is involved.

Experience and studies have shown that a number of what may be called second order effects are of substantial significance to the uniformity of the corneal section, and therefore to the qualitative results of the surgery itself. For example, an article entitled "Independent Evaluation of Second Generation Suction Microkeratomes", by Robert F. Hoffman, MD, et al., in *Refractive and Corneal Surgery*, Vol. 8, September/October 1992, pages 348–354, provides an analysis of three machines which were then current. All three machines were analyzed with respect to the accuracy of the thickness of the corneal flap, the smoothness of the corneal bed after the sectioning, and the appearance of irregularities in the corneal bed. Scanning electron micrographs, which provide high magnification images of the corneal bed, and high precision thickness measurement techniques were used to reveal deficiencies in each of three respects. The deficiencies were given in terms of "the accuracy of the resection diameter and thickness", "the ultrastructure of the resected stromo surfaces", and "the quality of the blades". In addition it is known that the cleaner the cut the faster the healing process. The eccentric action used to induce reciprocating motion was found to produce a periodic nonuniformity called "chatter", which was present in various degrees but always discernable. The vibratory motion imparted to the blade can also be understood to set up vibrations which propagate in different ways in the blade, and thus may give rise to resonances which cause deviations in the plane of the cut.

Nonetheless the requirements of the medical procedure dictate that each blade be handled individually for purposes of inspection, cleaning and final finishing. Even though the blade is honed and polished for maximum cutting efficiency, which is difficult to do, the blade itself is so thin that it may have imperfections, such as small bends or concavities that affect cutting of the corneal bed or lamellar flap. For example, a seemingly minor dip at the rear edge or in the interior body can be carried through to the cutting edge, affecting blade linearity. The more a blade must be handled during manufacture to assure flatness, smoothness and free of abrupt corners and edges other than the cutting tip, the greater the chance of this type of reduction of quality and uniformity.

What initially might appear to be a simple problem, in other words, has by such studies been revealed to involve much more complex and significant factors that affect both the optical correction and the efficacy of the healing process. Despite this understanding, basic blade and holder designs have remained largely unchanged and these problems are not known to have been addressed.

SUMMARY OF THE INVENTION

A cutting blade for microkeratomes in accordance with the invention is of conventional thinness, but configured with a geometry which minimizes the introduction of stress points and local nonuniformities in the course of manufacture, and the inherent resonances generated by vibration during reciprocation, and simplifies the process of manufacture to obtain a high yield during production.

In one example in accordance with the invention, the body of the blade is configured, apart from the linear cutting blade edge, to be substantially free of abrupt peripheral corners, with an arched posterior boundary edge. This configuration has a uniformity that reduces manufacturing complexities and a shape asymmetry which minimizes internal resonances when the blade is reciprocated. In addition, since there are no easily damaged edge protrusions, which can be bent or deflected much more readily than the blade body, there is less probability of stress risers, local discontinuities and other nonuniformities being introduced in handling and machining. In a principal configuration, the blade body apart from the cutting edge is of hemispherical outline, apart from a small opening leading into a coupling aperture used for attaching a blade driver or holder. The blade geometry can be combined with several different types of drivers, the differences in the blades being essentially only dimensional.

A typical blade in accordance with the invention has a cutting blade edge width in the range of 0.450" to 0.525" and a depth transverse to the cutting blade in the range of 0.200 to 0.350 inches, with a double beveled cutting blade tip of about 0.050", the blade itself will typically be of stainless steel and about 0.01" in thickness. The coupling aperture is ovoid in shape, centered in the body near the posterior edge, and elongated in a direction parallel to the cutting edge. An access slot along the center of the body from the posterior edge into the coupling aperture advantageously includes small geometrical indicia to identify the blade type.

The form factor of the blade holder, for a particular microkeratome instrument, is essentially dictated by the design of the instrument, but this does not foreclose adoption of features in the holder which improve cutting functions. The holder in each instance includes a planar base for seating against the surface of the blade, and a protruding boss matingly engaged into the coupling aperture. The slot for engagement of an eccentric drive pin is, from different machines, on the top or back surface of a slanted holder.

Methods in accordance with the invention commence with the lengthwise separation of a stock strip into a number of elongated strip blanks of surgical alloy, such as stainless steel. The strip blanks are ground along one edge on both sides to form a double bevel cutting edge terminating in a very sharp tip. The strip blanks are formed by longitudinally separating an initially 4 to 4½" wide stock strip into 4 or 5 smaller strip blanks. The strip blanks with cutting edges are sectioned longitudinally into blade blanks having at least one or preferably a number of different blade increments. These blade blanks are then held in fixtures and the posterior boundaries and coupling apertures are cut by electric discharge machining in an oil bath by motion control of a consumable electrode. This process also cuts the posterior boundary of the blade blank so that it includes, in the posterior central region a small slot perpendicular to the leading cutting edge that communicates with an interior ovoid coupling aperture. The slot is configured with an edge shape which uniquely identifies the blade type. The formed blade is then separated from the fixture and each individual blade is cleaned, inspected, and honed to provide a precisely flat, smooth broad face on each side. The arch of the posterior boundary wall between the ends of the anterior cutting tip can be mechanically abraded in a single motion. All steps subsequent to the formation of the cutting tip edge are undertaken without contact with that edge.

BRIEF DESCRIPTION OF THE DRAWINGS

A better understanding of the invention may be had by reference to the following description, taken in conjunction with the accompanying drawings, in which:

FIG. 1 is a perspective view, partially broken away, of a microkeratome blade and holder construction for use with a keratome having an eccentric pin that is mounted along a substantially vertical axis;

FIG. 2 is a side view of the arrangement of FIG. 1;

FIG. 3 is a plan view of the microkeratome blade used in the example of FIGS. 1 and 2;

FIG. 4 is an enlarged side view of the anterior portion of the microkeratome blade of FIGS. 1 and 2;

DETAILED DESCRIPTION OF THE INVENTION

Figure 5:
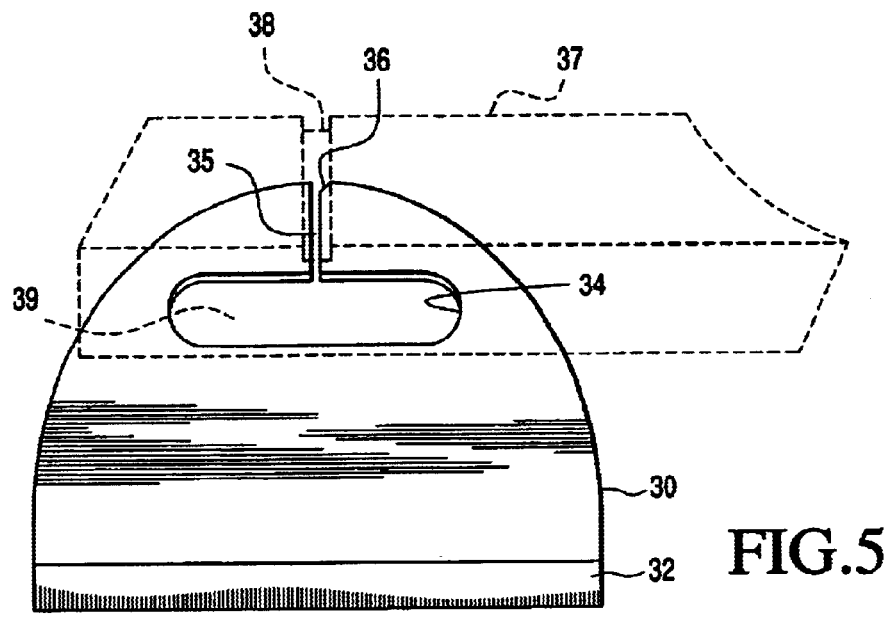
FIG. 5 is a perspective view of another blade having a posterior boundary of generally hemispherical outline, as used with a different type of blade holder in which the drive pin engages a side of the holder.

In the interest of brevity and simplicity, a detailed description is not provided herein of a microkeratome system with which the present invention may be used. Reference may be made to one of the above referenced patents for features of a typical microkeratome, bearing in mind that the Hellenkamp '009 patent on an arcuate path system is different in its drive mechanisms but still requires the precision and freedom from local nonuniformities and vibrating effects alluded to above. In FIGS. 1–3, the posterior boundary of a blade 10 is hemispherical in shape rearward of an anterior or leading cutting edge 12. The blade 10, which is of a surgical alloy, such as M-400 stainless steel, includes within its mid-region an ovoid aperture 14 that is open to the boundary through a small slot 15 in the blade 10 body. The slot 15 includes an indentation 16 which uniquely identifies the blade type. The holder 18, also called a driver, is a synthetic polymer element having a top surface 20 in which a slot or groove 21 is disposed perpendicular to the blade cutting edge 12. The bottom surface of the holder 18 is generally flat to engage against the upper surface of the blade 10, the cutting edge 12 of which is to shear through the thickness of the cornea at a selected depth and predetermined angle, seen generally in FIG. 2. The bottom of the driver or holder 18 includes a protruding coupling boss 23 which mates within the coupling aperture 14 in the blade 10. The boss 23 attaches the holder 18 to the blade 10 permanently or detachably, as by tight frictional fit, so it can be separately resterilized.

In the example of FIGS. 1–3, the blade cutting edge is 0.415" long, and the double bevel of the cutting tip is 0.05" deep, and converges at about 8°, preferably terminating at a sharper converging angle (6°) leading to the edge tip for a length of about 0.0015". The depth of the body between the anterior and posterior edges has a maximum dimension of 0.275" The processing sequence provides that the planar surface deviates less than 0.0001" from a nominal planar surface, and the cutting edge tip deviates less than 0.0002" from the nominal central plane of the body.

With this configuration, when lateral vibratory motion is induced in the holder 18 it is transmitted, via the boss 23 on the holder to the blade 10 itself. The resultant forces of oscillation acting on the blade 10 are directed laterally outward from the coupling apertures along the plane of the blade, through arcs centered about a line parallel to the cutting edge 12. The vibrations that traverse along the blade 10 are reflected at different local angles off the posterior periphery upon reaching the blade edge. Also, because the reciprocating pin in the drive mechanism moves up and down relative to the groove 21, these angles change during a cycle. Consequently, the vibrations do not tend to reinforce each other so as to build up at some resonance value. Thus, the primary energy from the vibration is expended along different path lengths and path directions as the blade reciprocates. Consequently, even if resonance modes exist that are not completely dissipated, the wave energy is still so low that distortion of the blade 10 is unlikely to introduce harmful displacement effects.

Another important advantage of this blade 10 is that since the hemispheric wall of the blade 10 is essentially continuous from side edge of the cutting blade 12 to the other, there is no inherently weaker part of the unit to be bent or deformed by contact during manufacture or assembly. The primary requisite for high blade quality is a precise, finely honed or finished cutting edge lying precisely along the plane of the blade. The number of processing and handling steps needed to machine, inspect and remachine until the desired exactness is achieved directly relates to the likelihood that irregularities will be introduced in the cutting edge, or that local deformities, such as bends or burrs, will be created in the body. Any local nonuniformity in the blade body can cause a minute wrinkling or crumpling at the cutting edge which can introduce unwanted deviations in the corneal bed. Since the semi-hemispherical shape has no protrusions or local areas which might deform more readily under stress, the body of the blade is less susceptible to such problems The blade of FIGS. 1–4 can be fabricated and finished with a high yield output, but still meet very high standards as to the critical parameters. The method enables high-rate production techniques to be used to advantage, together with the individual inspections imposed because of the critical importance placed on operative results with these surgical instruments.

In accordance with the invention, the methods that are employed commence with selection of an appropriate surgical alloy, such as stainless steel in a long stock strip of 4" to 4½" wide. This stock strip is longitudinally split or divided into 4 or 5 strip blanks that are then edge finished. For this, the strip blanks are ground along one edge on both sides to form the double bevel cutting edge terminating in the very sharp tip. The strip blanks with cutting edges are then divided longitudinally into blade blanks which may have one or preferably a number of different blade increments. Holding the blade blanks in fixtures which provide clearance for cutting the boundaries and coupling apertures, a stack of 200 blade blanks can be immersed in an oil bath. The contours of the blade are then defined by a computer controlled electric discharge machine head using a consumable electrode. This process cuts the posterior boundary of the blade blank as well as the coupling aperture and the small access slot in the posterior central region. The cutting edges of the blanks are not controlled and the dimensional controls are very precise. Then the fixture can be removed from the oil bath, the individual blades can be separated, and each inspected and cleaned. The blades are then honed to provide precisely flat, smooth broad face on each side, and the posterior periphery of the blades between the ends of the cutting tip can be abraded in a single motion, as by sanding to remove sharp edges and burrs.

Figure 6:
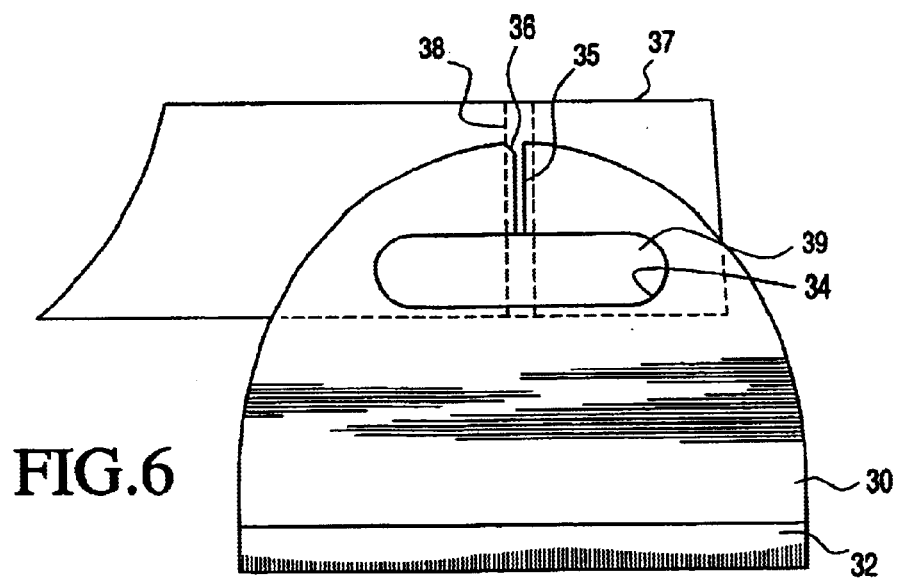
FIG. 6 is a plan view of the underside of the blade and holder in the arrangement of FIG. 5.

Referring now to FIGS. 5 and 6, the blade 30 disclosed therein includes a straight cutting edge 32 and generally hemispherical posterior periphery as previously described. Although designed for a different type of microkeratome instrument, the blade 30 also includes a single coupling aperture 34 that is ovoid and elongated substantially parallel to the cutting edge 32. The coupling aperture 34 is accessed via a small control slit 35 having a beveled corner 36 for blade type identification. An asymmetric holder 37 has an elongated groove 38 on one side for receiving a reciprocating drive pin (not shown) and a boss or protruding portion 39 on the other side mating to and engaging within the coupling aperture 34 to secure the holder 37 to the blade 30. Thus a generally hemispherical blade in accordance with the invention is amenable to use with totally different types of microkeratome machines. In the combination of FIGS. 5 and 6, the blade cutting edge width is 0.460", its maximum depth is 0.316", and the slot 35 leading to the coupling aperture 34. the blade thickness is 0.01", with a cutting edge taper of 0.050".

Figure 7:
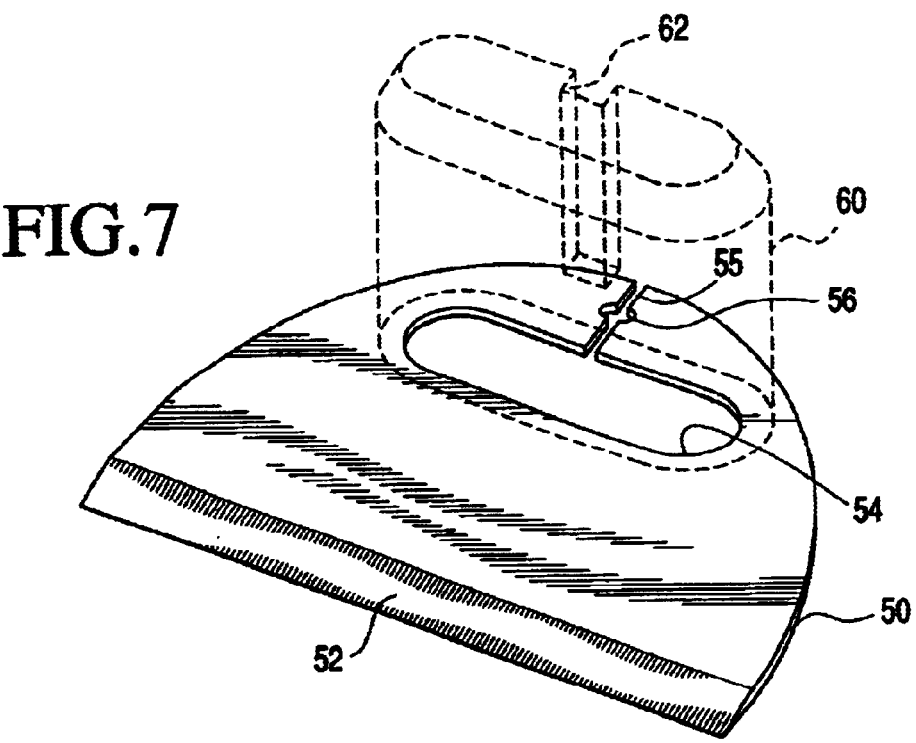
FIG. 7 is a perspective view of another blade and holder combination in which the drive pin engages a side of the holder.
Figure 8:
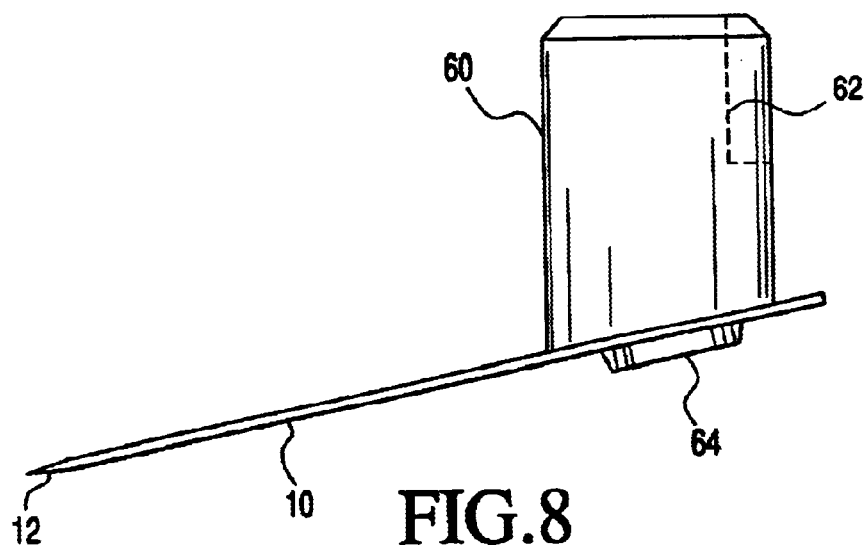
FIG. 8 is a side view of the combination of FIG. 7.

In the example of FIGS. 7 and 8, the blade 50 has a tip width of 0.508", a blade taper depth of 0.50" and an anterior-posterior depth of 0.315". Rearward of the cutting blade edge 52, the blade 50 includes an ovoid coupling aperture 54 which opens to the closest peripheral region through a small (0.015") central slot 55, including a pair of notch indicia 56 for identifying blade type. The holder or driver 60 has a side groove 62 for receiving the driver pin (not shown) of the instrument, and a protruding boss 64 that mates in the coupling aperture 54 of the blade 50. Although differing slightly in size and cooperating with a different instrument the advantages of the concept are nonetheless realized in full.

Other expedients will suggest themselves to those skilled in the art, in accordance with the various concepts and features proposed herein.

What is claimed is:

1. A microkeratome blade for tangential corneal incision with a reciprocating motion comprising:
   a cutting blade of stainless steel having a thin planar body of about 0.02" thick with an anterior linear boundary beveled with an angle of about 8 degrees and extending about 0.050" deep to a leading edge cutting tip, the anterior boundary being in the range of 0.450" to 0.525" long, the maximum anterior to posterior dimension being in the range of 0.250" to 0.400" deep, and including end corners at the limits thereof; and the cutting blade also including a substantially continuous curvilinear posterior boundary extending from one end corner of the anterior boundary to the other end corner in a generally hemispherical form, with the blade body also being formed to include an interior aperture that is adjacent the posterior boundary and elongated in a direction parallel to the anterior boundary.

2. A blade as set forth in claim 1 above further including a blade holder having a blade engaging surface including a boss extending therefrom and configured to mate within the holder retaining aperture of a central posterior position opening to the interior aperture from the posterior boundary and including a slot between the posterior boundary and the interior aperture having a unique configuration to identify the blade type.

* * * * *